(12) United States Patent
Qiu et al.

(10) Patent No.: US 11,697,655 B2
(45) Date of Patent: Jul. 11, 2023

(54) SYNTHESIS OF ERIBULIN MESYLATE

(71) Applicant: WISDOM PHARMACEUTICAL CO., LTD, Nantong (CN)

(72) Inventors: Xiaolong Qiu, Nantong (CN); Tao Xu, Nantong (CN); Zhiwei Zuo, Nantong (CN); Jie Ge, Nantong (CN); Xinwei Lu, Nantong (CN); Lingling Chu, Nantong (CN); Wenbo Liu, Nantong (CN); Biao Wang, Nantong (CN); Tingwei Gu, Nantong (CN); Weiwei Wang, Nantong (CN); Lin Hu, Nantong (CN); Ping Zou, Nantong (CN); Jun Chen, Nantong (CN); Lei Cao, Nantong (CN)

(73) Assignee: WISDOM PHARMACEUTICAL CO., LTD, Nantong (CN)

( * ) Notice: Subject to any disclaimer, the term of this patent is extended or adjusted under 35 U.S.C. 154(b) by 116 days.

(21) Appl. No.: 17/519,590

(22) Filed: Nov. 5, 2021

(65) Prior Publication Data
US 2022/0402933 A1 Dec. 22, 2022

Related U.S. Application Data

(63) Continuation of application No. PCT/CN2021/113477, filed on Aug. 19, 2021.

(30) Foreign Application Priority Data

Jun. 8, 2021 (CN) .......................... 202110638325.2

(51) Int. Cl.
*C07D 493/22* (2006.01)
(52) U.S. Cl.
CPC ........ *C07D 493/22* (2013.01); *C07B 2200/07* (2013.01)
(58) Field of Classification Search
CPC .......................... C07D 493/22; C07B 2200/07
See application file for complete search history.

(56) References Cited

FOREIGN PATENT DOCUMENTS

| CN | 1216051 C | 8/2005 |
|---|---|---|
| CN | 105916861 A | 8/2016 |
| CN | 109694379 A | 4/2019 |
| CN | 110922423 A | 3/2020 |
| WO | 2016031796 A1 | 3/2016 |

*Primary Examiner* — Susanna Moore
(74) *Attorney, Agent, or Firm* — Bayramoglu Law Offices LLC

(57) ABSTRACT

A preparation method of an intermediate compound of formula II ((1R,2S,3S,4S,5S,6R,11S,14S,17S,19R,21R,23S, 25R,26R,27S,31R,34S)-25-[(2S)-2,3-dihydroxy]-2,5-dihydroxy-26-methoxy-19-methyl-13,20-dimethylene-24,35,36, 37,38,39-hexaoxane[29.3.1.1$^{3,6}$.1$^{4,34}$.11$^{1,14}$.1$^{17,21}$.0$^{23,27}$] nonatriacontan-8,29-dione) for eribulin mesylate is provided, including subjecting a compound of formula I to a reaction with an additive in the presence of tetra-n-butylammonium fluoride (TBAF). The additive is piperidine hydrochloride or pyridine hydrochloride, and a reaction formula is as follows:

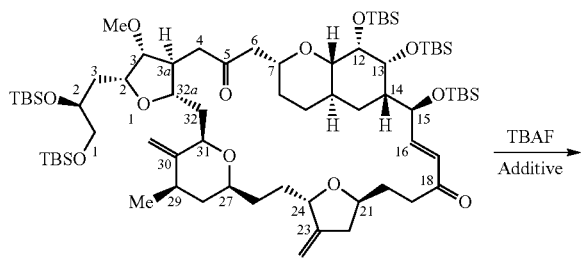

Formula I

2-[[(1,1-dimethylethyl)dimethylsilyl]oxy]-3-
[(2R, 3R, 3aS, 7R, 10S, 11S, 12S, 13R, 14S, 15S, 16E, 21S, 24S, 27S, 29R, 31R, 32aS)-12,13,15-tris[[(1,1-dimethylethyl)dimethylsilyl]oxy]-
3, 3a, 4, 5, 6, 7, 8, 9, 10, 11, 12, 13, 14, 15, 18, 19, 20, 21, 22, 23, 24, 25, 26, 27, 28, 29, 30, 31, 32, 32a-triahydro-3-methoxy-29-methyl-23, 30-bis(methylene)-5, 18-dioxo-7, 11:10, 14:21, 24:27, 31-tetraepoxy-2H-cyclohentriacontane[b]furan-2-yl]propyl]-1-[(I, 1-dimethylethyl)dimethyisily]ether

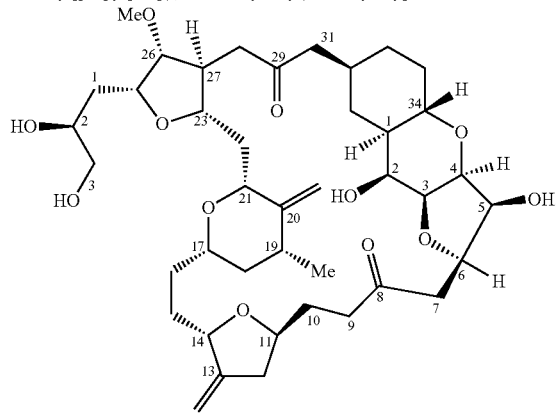

Formula II (1R, 2S, 3S, 4S, 5S, 6R, 11S, 14S, 17S, 19R, 21R, 23S, 25R, 26R, 27S, 31R, 34S)-25-[(2S)-2, 3-dihydroxy]-2, 5-dihyrdoxy-26-methoxy-19-methyl-13, 20-dimethylene-24, 35, 36, 37, 38, 39-hexaoxane [29.3.1.1$^{3, 6}$. 1$^{4,34}$. 11$^{1,14}$. 1$^{17, 21}$. 0$^{23, 27}$]nonatriacontan-8, 29-dione The present invention aims to avoid the problem that a traditional synthetic route has a low yield.

4 Claims, No Drawings

SYNTHESIS OF ERIBULIN MESYLATE

CROSS REFERENCE TO THE RELATED APPLICATIONS

This application is a continuation application of the International Application No. PCT/CN2021/113477, filed on Aug. 19, 2021, which is based upon and claims priority to Chinese Patent Application No. 202110638325.2, filed on Jun. 8, 2021, the entire contents of which are incorporated herein by reference.

TECHNICAL FIELD

The present disclosure belongs to the field of chemical synthesis, and specifically relates to a preparation of a key intermediate for eribulin mesylate (a complex natural modified drug).

BACKGROUND

Halichondrin B is a polyether macrolide isolated from the scarce Japanese sponge *Halichondria okadai* by Japanese scientists Uemura, et al. in the 1980s. Although halichondrin B only includes three elements of carbon, hydrogen, oxygen, the compound has a very complicated structure. Further research indicates that halichondrin B exhibits a very strong inhibitory effect on mouse cancer cells in vivo and in vitro in mouse experiments. Chemists further found through research that common sponges, such as *Phakellia, Lissodendory*, and *Axinella*, also include halichondrin B. The National Cancer Institute of the United States conducted a systematic activity evaluation of halichondrin B in 60 cancer cell lines, which has proved that the anti-cancer cell proliferation mechanism of halichondrin B is similar to that of known anti-microtubulin drugs, but biochemical mechanisms thereof are different, Due to the extremely strong activity and unique active mechanism, halichondrin B has attracted the attention of the academic and business circles. However, as a limited amount of samples can be isolated from sponges in the nature, the research and development is relatively slow. For this reason, a preparation of halichondrin B and analogues thereof by chemical synthesis has aroused the widespread interest of chemists. Halichondrin B has the following structure:

Professor Kishi of Harvard University systematically studied the total synthesis of halichondrin B and analogues thereof. A large number of studies have shown that, in the halichondrin B shown above, the right fragment is a carrier with higher anti-cancer activity than the polyether fragment on the left. This is because the right fragment includes a variety of functional groups, while the polyether fragment has a monotonous structure. These studies further allow synthetic chemists to prepare a series of halichondrin B analogues for activity test. Eribulin mesylate is one of halichondrin B analogues, which passed through the phase III clinical trial and was finally approved by the Food and Drug Administration (FDA) of the United States for the treatment of metastatic breast cancer (MBC) in 2010 under the trade name of HALAVEN™. A chemical structure of eribulin mesylate includes 19 chiral centers, and the chemical structure is as follows:

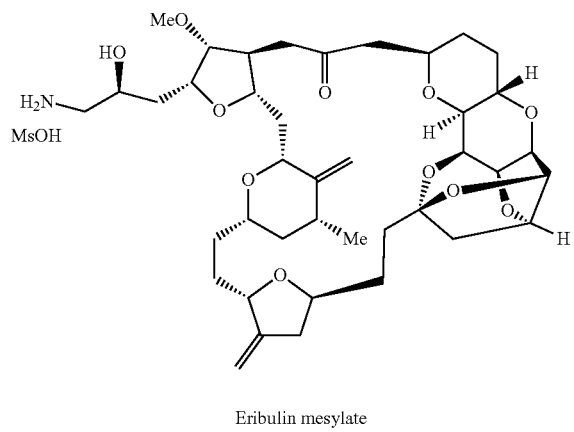 [SMILES: "MsOH" ; C=C1C[C@@H]2CC[C@@]34C[C@H]5O[C@H]6[C@@H](O3)[C@H]3O[C@H](CC[C@@H]3O[C@H]6[C@H]5O4)CC(=O)C[C@@H]3[C@@H](OC)[C@@H](C[C@H](O)CN)O[C@H]3C[C@H]3O[C@@H](CC[C@@H]1O2)C[C@@H](C)C3=C]

Eribulin mesylate

So far, the preparation of eribulin mesylate has been reported in a large number of patents and literatures. The current synthesis methods all involve how to realize the formation of a complex fused ring in the structure of eribulin mesylate. It is reported in literatures that the synthesis of eribulin mesylate includes: 5 tert-Butyldimethylsilyl (TBS) protecting groups are removed from an intermediate of formula I in the presence of tetra-n-butylammonium fluoride

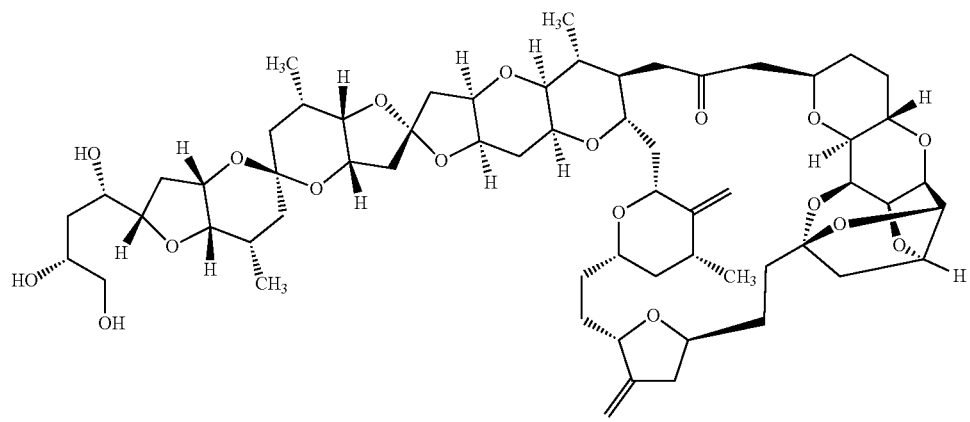

Halichondrin B (TBAF), and a hydroxyl group at the 13-position undergoes Michael addition with the α, β-unsaturated ketone in a molecule to produce a new furan ring to obtain a compound of formula II; in the compound of formula II, under the action of pyridinium p-toluenesulfonate (PPTS), two hydroxyl groups at the 2-position and 5-position undergo a dehydration and ketal reaction with the carbonyl group at the 8-position to obtain a compound of formula III; and a hydroxyl group on a side chain of the compound of formula III is subsequently converted into an amino group to obtain a mesylate salt, thereby realizing the preparation of eribulin mesylate. A specific reaction is as follows.

Studies have shown that the preparation of the compound of formula II by removing 5 TBS protecting groups from a compound of formula I (2-[[(1,1-dimethylethyl)dimethylsilyl]oxy]-3-[(2R,3R,3aS,7R,10S,11S,12S,13R,14S,15S,16E, 21S,24S,27S,29R,31R,32aS)-12,13,15-tris[[(1,1-dimethylethyl)dimethylsilyl]oxy]-3,3a,4,5,6,7,8,9,10,11,12,13,14,15,18,19,20,21,22,23,24,25,26,27,28,29,30,31,32,32a-triahydro-3-methoxy-29-m ethyl-23,30-bis(methylene)-5,18-dioxo-7,11:10,14:21,24:27,31-tetraepoxy-2H-cyclohentriacontane[b]furan-2-yl]propyl]-1-[(1,1-dimethylethyl)dimethylsilyl]ether) to form a furan ring has a yield only of about 40%. According to Chinese patent

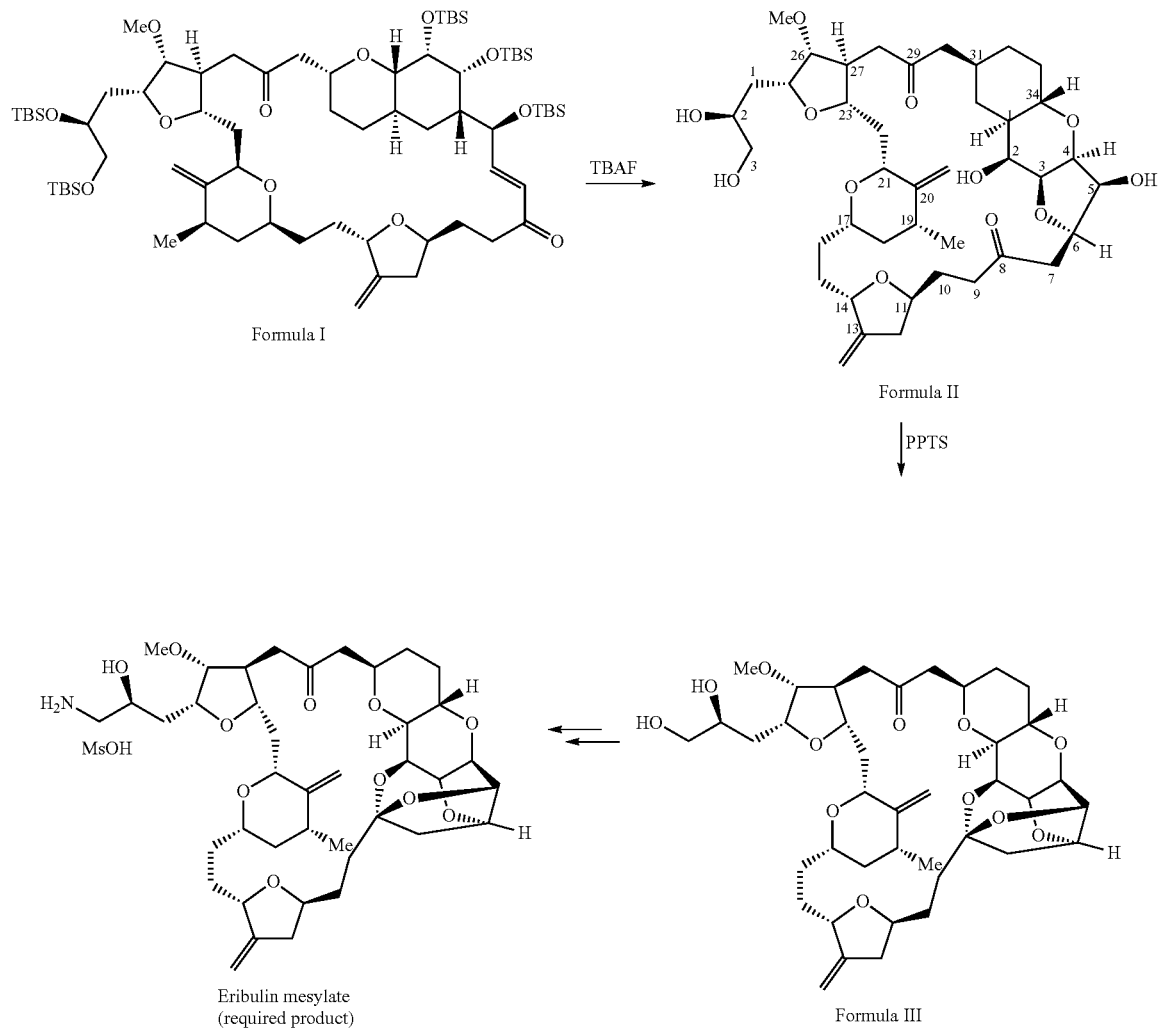

Formula I

Formula II

Formula III

Eribulin mesylate
(required product)

CN1216051C, the addition of imidazole hydrochloride to a reaction system can appropriately increase a yield of this step to about 60%. The experiment of adding imidazole hydrochloride in Chinese patent CN1216051C is reproduced, and it was found that the yield of this step is only about 50%. At present, a raw material for eribulin mesylate is very expensive, with a price of tens of thousands of dollars per gram. For this reason, how to improve a conversion yield of this step is of vital importance for the industrialization of eribulin mesylate and the price reduction of a final product.

SUMMARY

The present disclosure is intended to provide a preparation method of an intermediate compound of formula II for eribulin mesylate ((1R,2S,3S,4S,5S,6R,11S,14S,17S,19R, 21R,23S,25R,26R,27S,31R,34S)-25-[(2S)-2,3-dihydroxy]-2,5-dihydroxy-26-methoxy-19-methyl-13,20-dimethylene-24,35,36,37,38,39-hexaoxane[29.3.1 .1$^{3,6}$.1$^{4,34}$.11$^{1,14}$.1$^{17,}$ $_{21}$.0$^{23,27}$]nonatriacontan-8,29-dione), which aims to avoid the problem that a traditional synthetic route has a low yield.

A synthetic route of the present disclosure is as follows:

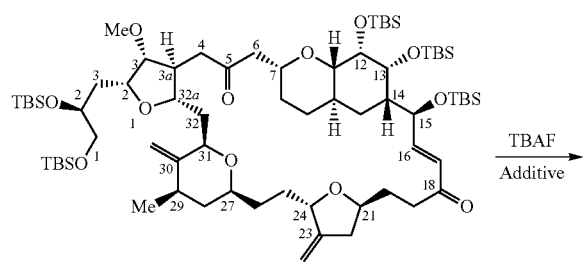

Formula I

2-[[(1,1-dimethylethyl)dimethylsilyl]oxy]-3-
[(2R, 3R, 3aS, 7R, 10S, 11S, 12S, 13R, 14S, 15S, 16E, 21S,
24S, 27S, 29R, 31R, 32aS)-12,13,15-tris[[(1,1-
dimethylethyl)dimethylsilyl]oxy]-
3, 3a, 4, 5, 6, 7, 8, 9, 10, 11, 12, 13, 14, 15, 18, 19, 20, 21,
22, 23, 24, 25, 26, 27, 28, 29, 30, 31, 32, 32a-triahydro-
3-methoxy-29-methyl-23, 30-bis(methylene)-5, 18-dioxo-7,
11:10, 14:21, 24:27, 31-tetraepoxy-2H-cyclohentriacontane[b]
furan-2-yl]propyl]-1-[(I, 1-dimethylethyl)dimethyisily]ether

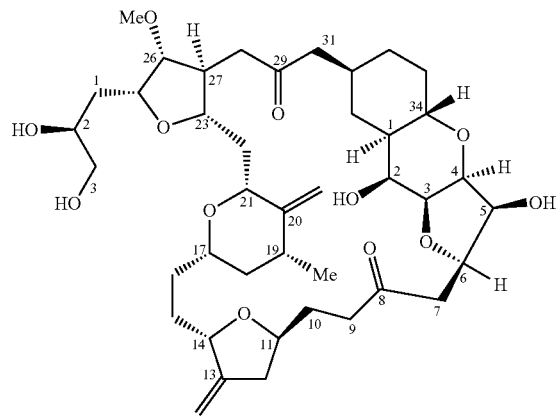

Formula II (1R, 2S, 3S, 4S, 5S, 6R, 11S, 14S, 17S, 19R, 21R, 23S, 25R,
26R, 27S, 31R, 34S)-25-[(2S)-2, 3-dihydroxy]-2, 5-
dihyrdoxy-26-methoxy-19-methyl-13, 20-
dimethylene-24, 35, 36, 37, 38, 39-hexaoxane
[29.3.1.1$^{3, 6}$. 1$^{4,34}$. 11$^{1,14}$. 1$^{17, 21}$. 0$^{23, 27}$]nonatriacontan-8, 29-
dione The synthetic route includes: additionally adding piperidine hydrochloride or pyridine hydrochloride to a reaction system of the compound of formula I in the presence of THF (as a solvent) and TBAF, which can effectively increase a conversion rate of formula I and thus improve a yield of formula II.

A specific implementation of the reaction includes: with THF as a solvent, adding TBAF (at a molar equivalent 5 to 20 times a molar equivalent of the compound of formula I) and piperidine hydrochloride or pyridine hydrochloride (at a molar equivalent 3 to 10 times a molar equivalent of the compound of formula I) to a reaction system, and conducting a reaction at 0° C. to 30° C. for 10 h to 30 h.

The present disclosure provides a new reaction additive, which can greatly improve a yield of the compound of formula II prepared from the compound formula I and is of great significance for the scale-up synthesis of eribulin mesylate with a complex structure.

DETAILED DESCRIPTION OF THE EMBODIMENTS

The present disclosure is illustrated below through typical examples, and simple replacements and improvements made by those skilled in the art to the present disclosure are all within the technical solutions claimed by the present disclosure.

Example 1 Preparation of a compound of formula II (using piperidine hydrochloride) (with a yield of 85%)

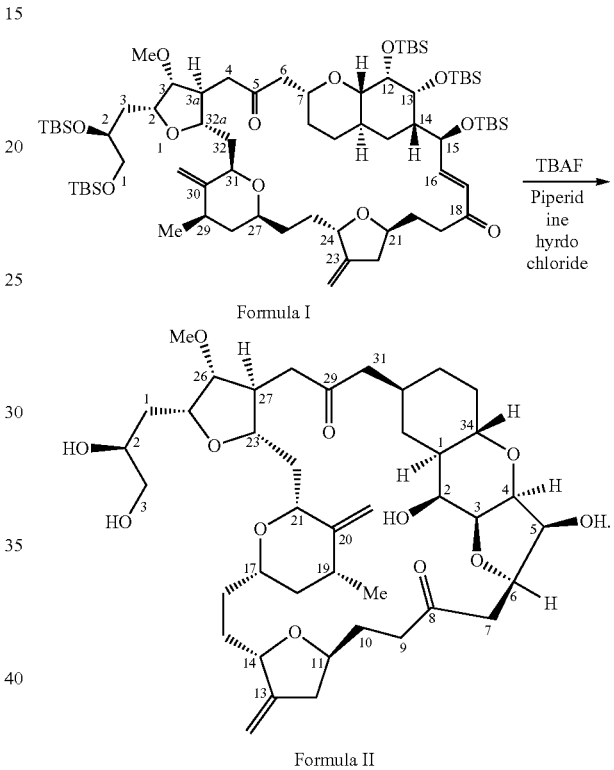

The compound of formula I (460.0 mg, 0.348 mmol) was dissolved in THF (21.5 mL) at 20° C. to 25° C., then piperidine hydrochloride (211.6 mg, 1.74 mmol) and TBAF (1 M THF solution, 3.48 mL, 3.48 mmol) were added, and a resulting reaction solution was stirred at the temperature for 20 h. The reaction solution was concentrated under reduced pressure at 30° C. to remove THF and then dissolved in a small amount of DCM, and then the target compound was purified and collected by column chromatography (EA/n-Hept=1/1→EA→MeOH/EA=1/15) to obtain the compound of formula II (white solid, 222.3 mg, 85.3%), ESI-MS: $C_{40}H_{60}O_{13}$: calculated value: 748.4034, measured value: 749.4065 (M+H$^+$).$^1$H NMR (600 MHz, CDCl$_3$)

5.00 (1H, brd, J=1.8 Hz), 4,85 (1H, brd, J=1.8 Hz), 4.88 (1H, brs), 4.80 (1H, brd, J=1.2 Hz), 4.48-4.54 (1H, m), 4.38 (1H, dd, $J_1$=9.0 Hz, $J_2$=4.2 Hz), 4.34 (1H, dt, $J_1$=10.2 Hz, $J_2$=3.6 Hz), 3.97-4.09 (5H, m), 3.94-3.99 (1H, m), 3.85-3.94 (3H, m), 3.78-3.85 (1H, m), 3.74 (1H, dd, $J_1$=9.6 Hz, $J_2$=1.8 Hz), 3.64 (1H, dd, $J_1$=11.4 Hz, $J_2$=3.6 Hz), 3.50-3.58 (1H, m), 3.40-3.46 (1H, m), 3.28-3.34 (1H, m), 3.30 (3H, s), 3.19 (1H, dd, $J_1$=15.0 Hz, $J_2$=10.2 Hz), 2.72-2.85 (2H, m), 2.49-2.69 (5H, m), 2.28-2.37 (2H, m), 2.14-2.30 (3H, m), 2.05-2.12 (1H, m), 1.98-2.05 (1H, m), 1.89-1.99 (2H, m), 1.64-1.81 (5H, m), 1.34-1.64 (5H, m), 1.03-1.13 (1H, m), 1.06 (3H, J=6.0 Hz). $^{13}$C NMR (150 MHz, CDCl3) 209.95, 208.71, 150.64, 149.04, 106.10, 104.85, 87.49, 82.53, 79.79, 79.57, 77.59, 77.40, 77.17, 76.83, 76.43, 75.97, 75.24, 73.57, 73.38, 71.08, 66.62, 65.80, 65.38, 56.94, 48.67, 47.91, 43.58, 42.89, 41.10, 40.93, 39.09, 37.71, 35.67, 32.57, 30.66, 30.51, 30.41, 30.09, 29.64, 17.89.

Example 2: Preparation of a compound of formula II (using pyridine hydrochloride) (with a yield of 89%)

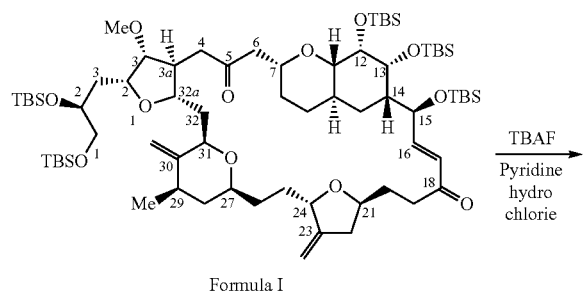
Formula I

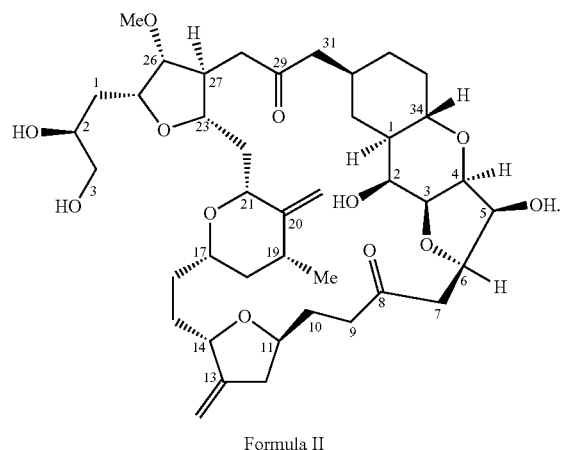
Formula II

The compound of formula I (460.0 mg, 0.348 mmol) was dissolved in THF (21.5 mL) at 20° C. to 25° C., then pyridine hydrochloride (201.1 mg, 1.74 mmol) and TBAF (1 M THF solution, 3.48 mL, 3.48 mmol) were added, and a resulting reaction solution was stirred at the temperature for 20 h. The reaction solution was concentrated under reduced pressure at 30° C. to remove THF and then dissolved in a small amount of DCM, and then the target compound was purified and collected by column chromatography (EA/n-Hept=1/1→EA→MeOH/EA=1/15) to obtain the compound of formula II (white solid, 232.1 mg, 88.9%).

Example 3: Preparation of a compound of formula II (comparative experiment, using only TBAF) (with a yield of 38%)

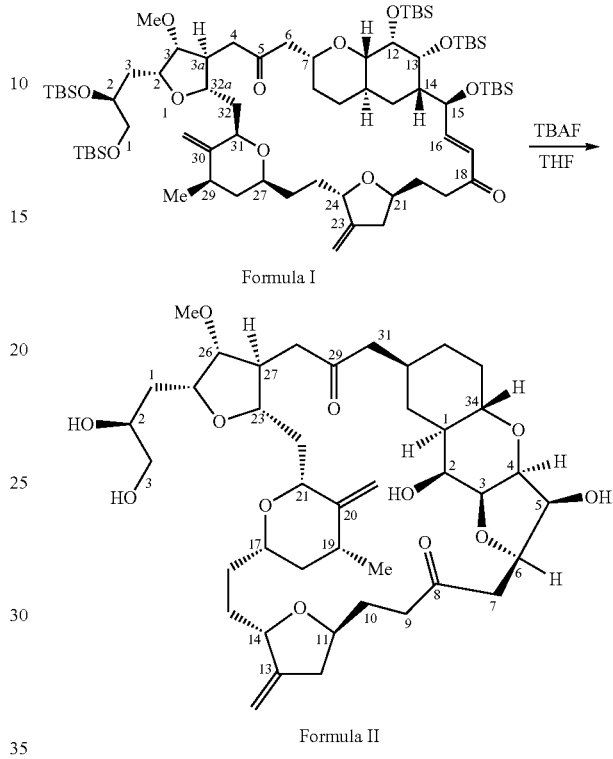
Formula I

Formula II

The compound of formula I (460.0 mg, 0.348 mmol) was dissolved in THF (21.5 mL) at 20° C. to 25° C., then TBAF (1 M THF solution, 3.48 mL, 3.48 mmol) was added, and a resulting reaction solution was stirred at the temperature for 20 h. The reaction solution was concentrated under reduced pressure at 30° C. to remove THF and then dissolved in a small amount of DCM, and then the target compound was purified and collected by column chromatography (EA/n-Hept=1/1→EA→MeOH/EA=1/15) to obtain the compound of formula II (white solid, 99.7 mg, 38.2%).

Example 4: Preparation of a compound of formula II (comparative experiment, using imidazole hydrochloride) (with a yield of 50%)

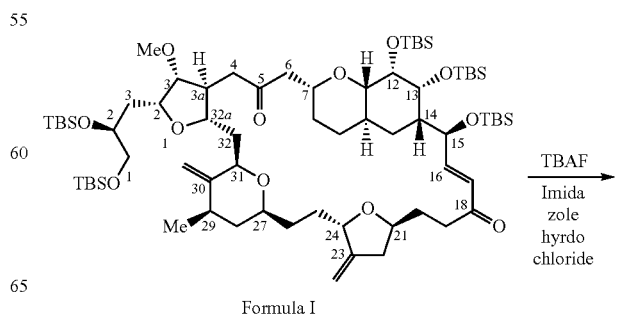
Formula I

-continued

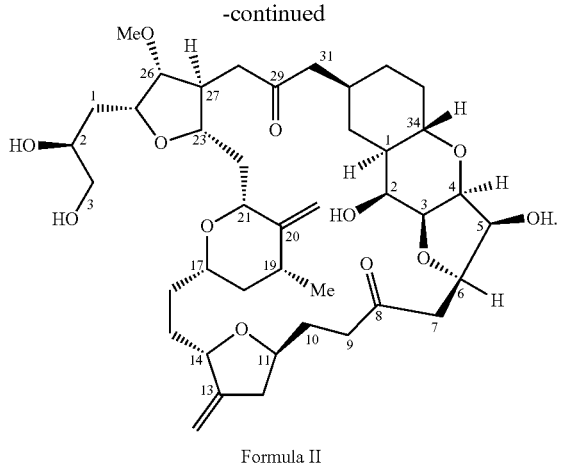

Formula II

The compound of formula 1 (460.0 mg, 0.348 mmol) was dissolved in THF (21.5 mL) at 20° C. to 25° C., then imidazole hydrochloride (181.9 mg, 1.74 mmol) and TBAF (1 M THF solution, 3.48 mL, 3.48 mmol) were added, and a resulting reaction solution was stirred at the temperature for 20 h. The reaction solution was concentrated under reduced pressure at 30° C. to remove THF and then dissolved in a small amount of DCM, and then the target compound was purified and collected by column chromatography (EA/n-Hept=1/1→EA→MeOH/EA=1/15) to obtain the compound of formula II (white solid, 131.5 mg, 50.4%).

What is claimed is:

1. A preparation method of an intermediate compound of formula II ((1R,2S,3S,4S,5S,6R,11S,14S,17S,19R,21R,23S, 25R,26R,27S,31R,34S)-25-[(2S)-2,3-dihydroxy]-2,5- dihydroxy-26-methoxy-19-methyl-13,20-dimethylene-24,35,36, 37,38,39-hexaoxane [29.3.1.1$^{3,6}$.1$^{4,34}$.11$^{1,14}$.1$^{17,21}$.0$^{23,27}$] nonatriacontan-8,29-dione) for eribulin mesylate, comprising:

subjecting a compound of formula I (2-[[(1,1-dimethylethyl)dimethylsilyl]oxy]-3-[(2R ,3R,3aS,7R,10S,11S, 12S,13R,14S,15S,16E,21 S,24S,27S,29R,31R,32aS)-12,13,15-tris[[(1,1-dimethylethyl)dimethylsilyl]oxy]-3,3a,4,5,6,7,8,9,10,11,12,13,14,15,18,19,20,21,22,23, 24,25,26,27,28,29,30,31,32,32a- triahydro-3-methoxy-29-m ethyl-23,30-bis(methylene)-5,18-dioxo-7,11:10, 14:21,24:27,31-tetraepoxy-2H-cyclohentriaconta ne[b] furan-2-yl]propyl]-1-[(1,1-dimethylethyl) dimethylsilyl]ether) to a reaction with an additive in the presence of tetra-n-butylammonium fluoride (TBAF), wherein the additive is piperidine hydrochloride or pyridine hydrochloride, and a reaction formula is as follows:

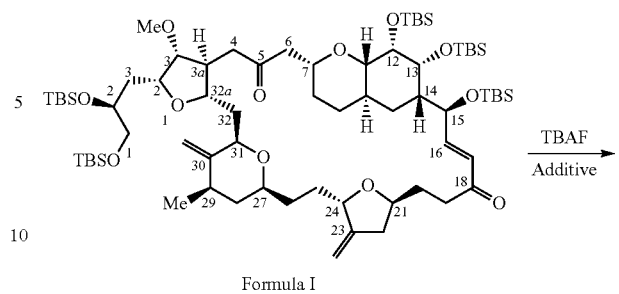

Formula I

2-[[(1,1-dimethylethyl)dimethylsilyl]oxy]-3-
[(2R, 3R, 3aS, 7R, 10S, 11S, 12S, 13R, 14S, 15S, 16E, 21S,
24S, 27S, 29R, 31R, 32aS)-12,13,15-tris[[(1,1-
dimethylethyl)dimethylsilyl]oxy]-
3, 3a, 4, 5, 6, 7, 8, 9, 10, 11, 12, 13, 14, 15, 18, 19, 20, 21,
22, 23, 24, 25, 26, 27, 28, 29, 30, 31, 32, 32a-triahydro-
3-methoxy-29-methyl-23, 30-bis(methylene)-5, 18-dioxo-7,
11:10, 14:21, 24:27, 31-tetraepoxy-2H-cyclohentriacontane[b]
furan-2-yl]propyl]-1-[(I, 1-dimethylethyl)dimethyisilyl]ether

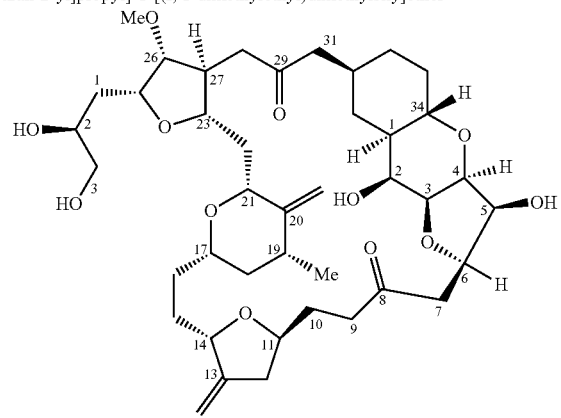

Formula II (1R, 2S, 3S, 4S, 5S, 6R, 11S, 14S, 17S, 19R, 21R, 23S, 25R,
26R, 27S, 31R, 34S)-25-[(2S)-2, 3-dihydroxy]-2, 5-
dihyrdoxy-26-methoxy-19-methyl-13, 20-
dimethylene-24, 35, 36, 37, 38, 39-hexaoxane
[29.3.1.1$^{3, 6}$. 1$^{4,34}$. 11$^{1,14}$. 1$^{17, 21}$. 0$^{23, 27}$]nonatriacontan-8, 29-dione.

2. The preparation method according to claim 1, wherein the TBAF is used at a molar equivalent 5 to 20 times a molar equivalent of the compound of formula I.

3. The preparation method according to claim 1, wherein the piperidine hydrochloride or the pyridine hydrochloride is used at a molar equivalent 3 to 10 times a molar equivalent of the compound of formula I.

4. The preparation method according to claim 1, wherein the reaction is conducted at 0° C. to 30° C.

* * * * *